United States Patent
Vilsmeier

(10) Patent No.: US 9,195,798 B2
(45) Date of Patent: Nov. 24, 2015

(54) FLEXIBLE COMPUTATION OF ISODOSE LINES

(75) Inventor: Stefan Vilsmeier, München (DE)

(73) Assignee: Brainlab AG, Feldkirchen (DE)

( * ) Notice: Subject to any disclaimer, the term of this patent is extended or adjusted under 35 U.S.C. 154(b) by 352 days.

(21) Appl. No.: 13/411,674

(22) Filed: Mar. 5, 2012

(65) Prior Publication Data

US 2013/0229432 A1   Sep. 5, 2013

(51) Int. Cl.
*G09G 5/30* (2006.01)
*G06F 19/00* (2011.01)
*A61N 5/10* (2006.01)

(52) U.S. Cl.
CPC .......... *G06F 19/3406* (2013.01); *G06F 19/321* (2013.01); *A61N 5/103* (2013.01)

(58) Field of Classification Search
CPC ........................................................ A61N 1/00
USPC ........................................................ 345/629
See application file for complete search history.

(56) References Cited

U.S. PATENT DOCUMENTS

| | | | | |
|---|---|---|---|---|
| 3,871,579 A * | 3/1975 | Inamura | | 378/108 |
| 5,027,818 A * | 7/1991 | Bova et al. | | 600/427 |
| 5,547,454 A * | 8/1996 | Horn et al. | | 600/1 |
| 5,851,182 A * | 12/1998 | Sahadevan | | 600/407 |
| 2012/0004492 A1* | 1/2012 | Weibrecht et al. | | 600/1 |
| 2012/0121068 A1* | 5/2012 | Maurer et al. | | 378/62 |
| 2012/0157746 A1* | 6/2012 | Meltsner et al. | | 600/1 |
| 2012/0252883 A1* | 10/2012 | Kolesnick et al. | | 514/44 R |
| 2013/0085387 A1* | 4/2013 | Chen et al. | | 600/439 |
| 2013/0090549 A1* | 4/2013 | Meltsner et al. | | 600/411 |
| 2013/0113802 A1* | 5/2013 | Weersink et al. | | 345/427 |
| 2013/0130991 A1* | 5/2013 | Widmann et al. | | 514/19.3 |
| 2013/0245425 A1* | 9/2013 | Dempsey | | 600/411 |
| 2013/0315463 A1* | 11/2013 | Vilsmeier et al. | | 382/131 |

OTHER PUBLICATIONS

Journal of Applied Clinical Medical Physics, vol. 11, No. 2 (2010); Christopher J. Anker a, Brian Wang, Matt Tobler, Julie Chapek, Dennis C. Shrieve, Ying J. Hitchcock, Bill J. Salter "Evaluation of fluence-smoothing feature for three IMRT planning systems".*

May 9, 2005; Computing Isodose Curves for Radiotherapy Treatment Plans; Ryan Acosta; Trinity University.*

* cited by examiner

*Primary Examiner* — Javid A Amini
(74) *Attorney, Agent, or Firm* — Tucker Ellis LLP

(57) ABSTRACT

The present invention relates to a data processing method of determining a distribution of isolines to be used for displaying a radiation dose distribution in tissue of a patient, the steps of the method being executed by a computer and comprising:
d) acquiring dose distribution data comprising dose distribution information describing a radiation dose distribution in an anatomical body part;
e) acquiring display data comprising display information describing a predetermined display mode to be applied for displaying the dose distribution information;
f) determining, based on the dose distribution data and the display data, isodose data comprising isodose information describing a distribution of is isolines to be used for displaying the dose distribution information.

13 Claims, 5 Drawing Sheets

FLEXIBLE COMPUTATION OF ISODOSE LINES

The present invention is directed to a method, in particular data processing method of determining a distribution of isolines to be used for displaying a radiation dose distribution according to the independent claim.

BACKGROUND

When planning a radiotherapy treatment for a specific patient, the distribution of the radiation dose in tissue of the patient's body is generally determined before the treatment starts. In general, a graphical display of a dose distribution is displayed within medical image information about the anatomical region of interest. The region of interest comprises a target region and off-target regions such as healthy tissue and critical structures. The information about the dose distribution is normally displayed by using a scheme of isodose lines located at predetermined (i.e. fixed) dose intervals. This may lead to problems in visually differentiating between different isodose lines in case they are situated so close to one another in a specific display mode that an operator's eye or mind cannot discern between different lines or that the operator regards the presentation as leading to discomfort when viewing it.

SUMMARY OF THE INVENTION

The present invention enables creation of a display mode for easier visual recognition of different, in particular neighbouring, isodose lines.

More particularly, the present invention provides a data processing method of determining a distribution of isolines to be used for displaying a radiation dose distribution in tissue of a patient, the steps of the method being executed by a computer and comprising:
 a) acquiring dose distribution data comprising dose distribution information describing a radiation dose distribution in an anatomical body part;
 b) acquiring display data comprising display information describing a predetermined display mode to be applied for displaying the dose distribution information; and
 c) determining, based on the dose distribution data and the display data, isodose data comprising isodose information describing a distribution of isolines to be used for displaying the dose distribution information.

Advantages, advantageous features, advantageous embodiments and advantageous aspects of the present invention are disclosed in the following and contained in the subject-matter of the claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

In order to determine the position of or visualize the anatomical region of interest, analytical devices such as x-ray devices, CT devices or MRT devices are used to generate analytical images (such as x-ray images or MRT images) of the body. Analytical devices are in particular devices for analysing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (in particular, internal structures and/or anatomical parts of the patient's body) by analysing the body. Analytical devices are in particular used in medical diagnosis, in particular in radiology.

In the field of medicine, imaging methods (also called medical imaging methods) are used to generate image data (for example, two-dimensional or three-dimensional image data) of anatomical structures (such as soft tissues, bones, organs, etc.) of the human body. Image data created by using medical imaging methods is therefore also termed medical image data. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. The MRI scans represent an example of an imaging method.

The method in accordance with the invention is in particular a data processing method. The data processing method is preferably performed using technical means, in particular is a computer. In particular, the data processing method is executed by or on the computer.

The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

Preferably, the inventive method is at least partly executed by a computer. That is, all steps or just some of the steps (i.e. less than a total number of steps) of the inventive method may be executed by a computer.

The inventive method is a data processing method of determining a distribution of isodose lines to be used for displaying a radiation dose distribution. The radiation dose distribution represents information about the distribution of a radiation dose accumulated in tissue of a patient due to irradiation with ionizing radiation, in particular due to radiotherapy. In the framework of this disclosure, the term of dose encompasses both the term of energy dose and equivalent dose. Preferably, medical image data is acquired which comprises medical image information describing an anatomical body part of the patient. Medical image data is image data which is produced by applying a medical imaging method to the patient's body.

Preferably, dose distribution data is acquired which comprises dose distribution information describing a radiation dose distribution in the anatomical body part which comprises a region of interest. Preferably, the dose distribution data is acquired based on the medical image data. In particular, absorption data comprising absorption information describing an absorption of the treatment radiation by the anatomical body part may be acquired based on the medical image data. The dose distribution information therefore preferably comprises positional information about an assignment of dose values to a position in the anatomical body part (the region of interest). The absorption information acquired based on the medical image data is preferably represented by Hounsfield units which are a measure of absorption of the ionizing radiation used for the imaging method with which the medical image data are generated in relation to the image contrast, in particular in relation to its grey shades. By providing information about the type of treatment radiation and in particular the beam energy, the corresponding absorption of the treatment radiation by the anatomical body part may be determined. The dose distribution data then is preferably acquired based on the absorption data. Alternatively, the dose distribution data is predetermined and merely acquired by the inventive method.

Preferably, the dose distribution information (and, further preferably, also the medical image information) is displayed on a display device. Further preferably, the dose distribution information is displayed in the medical image information, in particular by overlaying it on the medical image information. The display device in particular is any kind of standard monitor (which in particular has a screen) such as a cathode ray tube monitor or an LCD display, more particularly any kind of screen device such as a screen device of a hand-held computer device such as a mobile phone (e.g. a smartphone). Displaying the dose distribution information is preferably based on using a colour range for the highlighting which represents information about the dose values. In particular, specific dose values (and/or specific dose value intervals) are uniquely assigned specific colours (also called colour values). The dose distribution information is preferably displayed such that it is displayed at a specific location of the region of interest in the image. In other words, the dose distribution preferably is graphically overlaid over the graphical representation of the body part for which it has been determined and with which it is associated, i.e. it is overlaid on the medical image infomration.

A colour range is a range or interval of distinct colour values which each appear only once in the interval. The colour value is preferably defined in a colour space such as a red-green-blue (RGB) colour space or a cyan-magenta-yellow-black (CMYK) colour space.

Preferably, the colour values in the colour range are normalized to represent a dose distribution value range which is unique to the colour range. For example, different dose distribution value ranges as described by the dose distribution information may be displayed with different, in particular disjoint, colour ranges.

Information about the colour range, in particular the colour values contained in the colour range, is preferably described by colour range information contained in colour range data. In other words, the colour range information describes a colour range usable for displaying dose distribution information, in particular dose values. More particularly, the colour range (the colour values) describes dose values. The colour range data is preferably acquired within the inventive method. The dose distribution data then is preferably displayed based on (also) the colour range data.

Preferably, dose value range data is determined based on acquiring a maximum and a minimum dose value contained in the dose distribution information. The dose value range data in particular comprises dose value range information which describes a range of dose values to be displayed. Preferably, colour range partition data is acquired or determined based on the dose value range data. The colour range partition data in particular comprises partition information which describes a partitioning of the dose distribution range. Preferably, the dose distribution range is partitioned into disjoint classes or discrete values. Each disjoint class or discrete value is then assigned a colour value in the colour range. Alternatively or additionally, the dose distribution range is partitioned by dividing it into classes describing a percentage (or percentage interval) of the dose values relative to a predetermined, such as desired (in particular, therapeutic) dose. The dose distribution information is then preferably displayed based on the colour range partition data.

Preferably, display data is acquired which comprises display information. The display information in particular describes a predetermined display mode to be applied for displaying the dose distribution information and, preferably, also the medical image information. In particular, the display information comprises graphical resolution information which describes a graphical resolution of a display device to be used for displaying the dose distribution information such as the size of an image element, in particular of a pixel. The image element in particular is an image element provided by the display device on which the dose distribution information shall be displayed. The information about the size of the image element is, for example, acquired from information stored in the display device itself or provided to the inventive method as a predetermined value, in particular based on determining the type of display device on which the dose distribution information is to be displayed.

Preferably, the inventive method then carries on with determining, based on the dose is distribution data (in particular, the dose distribution information) and the display data (in particular, the display information), isodose data comprising isodose information. The isodose information in particular describes a display mode for displaying the dose distribution information, in particular a distribution of isolines. Preferably, the dose distribution information is displayed as isodose lines, i.e. a line diagram using isolines which represent specific dose values or dose value intervals described by the dose distribution information. Preferably, the isolines are each assigned a unique colour value in order to support a colour range-based display of the dose distribution information. The distribution of the isolines describes at least one of the number of isolines distributions and the distance between isolines (i.e. their spacing), in particular between each pair of neighbouring isolines (i.e. between two isolines lying next to one another, in particular two isolines representing closest neighbours). Preferably, the number of isolines to be used for displaying the dose distribution information (i.e. the number of isolines to be displayed) is determined based on the display data. The number of isoline in particular is a number of isolines for displaying the dose values located in a specific interval, such as a maximum dose value and a minimum dose value to be displayed for the anatomical body part. In particular, the maximum and minimum dose values are the maximum and minimum dose values described by the dose distribution information. Since each isoline represents a specific dose value or dose value interval, the isolines are also called isodose lines. The dose values (dose value intervals) represented by each isodose line in general varies with the number of isolines to be used for displaying dose values (dose value intervals) lying in a specific range of dose values. Determining the number of isolines to be used thus in particular also comprises determining the dose values (dose value intervals) which are associated with each of the isolines. According to the invention, however, the number of isolines is determined first based on i.a. the display data and a range of dose values to be considered, and the dose values (dose value intervals) to be assigned to each isoline are determined based on the number of isolines to be used. Such a procedure appears to be advisable since the inventive method aims at providing an advantageous display mode rather than displaying specific dose values which are, for example, spaced at predetermined distances from one another.

Preferably, the display information comprises spacing information also referred to as graphical distance information which describes a spacing, for instance a predetermined graphical distance between each pair of neighbouring isolines to be used for displaying the dose distribution information. The predetermined spacing is in particular described as a function of distance maximum distance, in particular between neighbouring isolines or as a function of an area between neighbouring isolines. In the following, the expressions "predetermined graphical distance" or "graphical distance" are just used as an example for the different possible implementations of the "predetermined spacing" or "spacing" respectively. The term "average" can mean herein for instance median, mean or mode. Preferably, the number of isolines to be used is determined based on the graphical distance, in particular a pixel distance between neighbouring isolines. The spacing (the graphical distance) is in particular defined as an average number of pixels lying inbetween two neighbouring isolines in the display mode or the spacing can be defined as the total number of pixels lying inbetween the neighbouring isolines (which corresponds to the area inbetween). Preferably, the absolute size of a pixel is known from information acquired from the display device so that a pixel distance alternatively or additionally also describes an absolute distance between two neighbouring isolines. The number of isolines to be used is preferably determined based on the result of determining whether the graphical distance, in particular absolute distance, between two isolines to be used preferably is greater or equal to a minimum graphical distance (in particular, minimum absolute distance), in particular the minimum graphical distance between any pair of points on the neighbouring isolines (i.e. any pair of points having each one point) lying on each one of the neighbouring isolines), which preferably has a predetermined value, in particular a value of at least one, preferably at least three millimeters so that the human eye is able to easily discern between two displayed neighbouring isolines. The inventive method preferably has a step of determining, based on the graphical distance information, whether in the set of isolines to be used, at least two neighbouring isolines have a graphical distance which is less than the predetermined graphical distance, the predetermined graphical distance being preferably at least three millimeters. The graphical distance encompasses any kind of distance measure for defining a distance between features of a graphical display, i.e. between image features. The distance may, for example, be determined by adding up the number of pixels which are intersected by a straight line connecting the image elements (in particular, points lying on neighbouring isolines, in particular isodose lines) in particular by using the shortest way of connection or by using a metric (such as a Euclidean metric in two or three dimensions) between two image features. The image features between which the graphical distance is to be determined may for example be defined as pixels which are intersected by (i.e. lie on) an isoline. The distance between two isolines may thus be determined by determining the graphical distance between a pixel lying on an isoline and shortest distance to a pixel lying on a neighbouring isoline (i.e. the distance to the closest pixel lying on a neighbouring isoline). As noted, the graphical distance may be expressed as number of pixels lying inbetween the image features (e.g. lying in the line of connection) or as an absolute distance, the absolute distance depending on in particular the size of pixels of the specific display device and can be in particular expressed in a (metric) unit like mm.

If it is determined that at least two neighbouring isolines have a graphical distance from one another below the predetermined graphical distance, the inventive method preferably reduces the number of isoline to be used. In particular, such a reduction is conducted if it is determined that not all of the isolines to be used have a predetermined graphical distance from each neighbouring isoline. The isodose data (in particular, the distribution of isolines) is then re-determined such that the number of isolines to be used is determined based on the condition that all isolines to be used have a graphical distance between each two neighbouring isolines which on average is the same for all of the isolines. Thus, not only the number of isolines is re-computed but also the dose values (dose intervals) associated with each isoline are adapted to the re-computed number of isolines. Thereby, a display mode for displaying the dose distribution information is supported which is both comfortable and attractive to an operator. In particular, generating isolines which, for the whole set of isolines, have on average the same distance to their neighbours along the whole of their circumference leads to a harmonic display which avoids distraction of the operator's attention to specific parts of the display. Furthermore, the information which is displayed and has to be processed by the operator's mind is reduced to a minimum of required information as a function of graphical boundary conditions and a number of dose values (dose value intervals) to be displayed as a start condition for the inventive method. The number of isolines to be used, which number is acquired by the inventive method as a start condition, preferably is lower than 15 or 12 or 10 and higher than 2 or 3 or 4 and is preferably 7, however also a number lower or higher than seven may be used to the start condition. Computational resources permitting, a number of more than seven isolines may be used as a start condition. The start condition in particular is a start condition for determining whether all of the isolines to be used fulfil the criterion of predetermined graphical distance to their neighbouring isolines. If this is already the case for the initial set of isolines, the number of isolines is not varied and the initial set of isolines is accepted for being displayed. If this is not the case, the number of isolines to be used is reduced as explained above.

If it is determined that all neighbouring isolines have a graphical distance from one another which is at least the predetermined (minimum) graphical distance (i.e. greater than or equal to the predetermined graphical distance), the inventive method preferably carries out a step of determining whether the number of isolines to be used can be increased while ensuring that, due to such an increase in the number of isolines, the graphical distance between neighbouring isolines does not become less than the predetermined graphical distance. As long as the condition of the graphical distance between neighbouring isolines is fulfilled for each pair of neighbouring isolines, a number of isolines to be used is increased preferably until in particular a predetermined maximum number of isolines to be used is reached. A maximum number of isolines to be used preferably is 7, higher or lower numbers are within the framework of the invention, though. In particular, the maximum number is higher than 4 and far lower than 12. A threshold average graphical distance between neighbouring isolines at or above which the inventive method determines whether the number of isolines can be increased may be the same as the minimum graphical distance or have a value different from, in particular greater than, the minimum graphical distance, for instance more than 10% greater and/or less than 100% greater.

Preferably, a further condition for varying, in particular reducing or increasing, the number of isolines, is a zoom factor applied to the medical image information. For example, the number of isolines to be used may also be determined based on such a zoom factor. In particular, a higher zoom factor may allow displaying isolines at smaller isoline value intervals (i.e. at smaller intervals of associated dose values) on the same display area used for displaying the medical image information. If the zoom factor is reduced, i.e. an operator zooms out of the image, the number of isolines per absolute area of the anatomical body part is preferably reduced (in particular, by increasing the isolines value intervals) in order to avoid graphical overcrowding of the image with isolines. Preferably, the number of isolines is only increased (in particular, by reducing the isoline value intervals) if the inventive method determines the display of the anatomical body part in the display mode constitutes (at least) a predetermined percentage or absolute amount of the display area of the medical image information. Preferably, the distribution (in particular number) of isolines is determined (in particular optimized) based on the zoom factor so that the isoline value intervals are suitable for the dose value range associated with the medical image information displayed at that zoom factor. The display area for example depends on the absolute size (in particular, pixel area or area in absolute measures) of a display window in which the medical image information is displayed. Thus, if a specific zoom factor is reached, the number of isolines is preferably not reduced anymore in order to avoid that no isoline at all is displayed. A predetermined zoom factor may therefore be used as a threshold zoom factor, at or above which a number of isolines is only kept fixed or increased rather than reduced. Furthermore, the number of isolines to be used is preferably determined based on the absolute size of a display area (measured in pixels), in particular a display window, in which the medical image information is displayed. In particular, the number of isolines to be used increases with increasing size of the display area and decreases with decreasing size of the display area. The display area may be divided in sub-areas, which for example is the case if a display window comprises a number of different views of the medical image information, each sub-area being used for each a different view. The larger the number of sub-areas, the smaller the size of a sub-areas gets compared to the overall size of the display window. The number of isolines to be used in the display of a single sub-area (view) therefore in particular depends on the ratio of the absolute size of the sub-area (view) to the absolute size of display area. Therefore, the number of isolines to be used may also be determined based on the number of sub-areas contained in the display area, in particular based on the number of views contained in the display window. In particular, the number of isolines to be used increases with decreasing number of sub-areas (views) and decreases with increasing number of sub-areas (views).

Between neighbouring isolines, a colour shading is plotted preferably with a colour value similar to the colour value which is assigned to the respective isodose line of the neighbouring isolines representing the lower dose value. With increasing zoom level, the saturation of the colour shading decreases, i.e. the colour shading becomes more transparent in order to allow an operator to recognize more details of the underlying medical image information.

The isodose lines preferably are isolines representing a predetermined percentage of a desired dose value to be applied to the anatomical body part, in particular to a target region. There may also be isodose lines associated with a dose value of more than the desired dose since it is known that irradiation of human tissue with ionizing radiation may lead to creation of so-called hotspots. Hotspots are individual and preferably isolated (discrete) parts of the anatomical body part to be irradiated in which abnormally high doses are accumulated, for example parts having a higher blood perfusion than other parts of the anatomical body part (such as parts of a tumour or blood vessels). It is desirable to visualize a location of such hotspots. For example, an isodose line delimiting regions in the anatomical body part in which a predetermined dose value which is in particular higher than the desired dose value is accumulated. In presently known algorithms, such hotspots are either not determined or defined as having at least a predetermined absolute dose value (critical dose) above which the presence of a hotspot is determined. Using such a fixed, predetermined critical dose value, it may happen that meaningless apparent (unreal or false) hotspots are determined if e.g. the critical dose value is below the desired dose value. Thus, a need arises for a more flexible manner of determining hotspots. This object is achieved by the method features described in the following, which can be understood to constitute an invention of its own. However, the following method features may also be combined with the aforementioned method features.

Preferably, critical dose data is determined which comprises critical dose information. The critical dose information in particular describes a desired dose. The critical dose is preferably determined based on determining a predetermined percentage of a difference between the maximum dose value described by the dose distribution information and the predetermined, in particular desired dose value described by the dose distribution information, and adding the predetermined percentage of the difference to the predetermined, in particular desired dose value. In other words, the following equation (1) is preferably applied for determining the critical dose information:

$$\text{critical dose} = [(\text{maximum dose}/\text{desired dose} \cdot 100\% - 100\%) \cdot c + 100\%] \cdot \text{desired dose} \qquad (1)$$

$c$ is a predetermined constant which defines the relative distance of the critical dose from the desired dose. $c$ preferably less than 1 or 0.9 and preferably more than 0.4 or 0.5 or 0.6, in particular the value is 0.8, however other values are also envisaged. $c=0.8$ is preferably chosen since it leads to a significant area in the displayed dose distribution information and therefore already a visual impression on the operator which may be used to roughly determine the distance of the critical dose from the desired dose. Depending on the pathologic condition to be assessed with respect to a specific patient, $c$ may also be chosen to be $c=0.6$. Preferably, the critical dose is visualized as an isoline representing a critical isodose line. The critical isodose encircles a region of the anatomical body part associated with dose values having at least the dose value represented by the critical dose. Therefore, a visual comparison of the area enclosed by the critical isodose line and the area enclosed by the neighbouring isodose line (representing in particular the next lower isodose value to be displayed, in particular the desired dose value) may lead to the following rough conclusions for an operator: If the area enclosed by the critical isodose line is comparably large to the area enclosed by the neighbouring isodose line, the operator may roughly conclude that the maximum dose associated with a hotspot is comparably close to the desired dose. If the area enclosed by the critical isodose line is small compared to the area enclosed by the neighbouring isodose line, the operator may roughly conclude that there are only isolated hotspots which in particular present a dose value which is comparably large with respect to the desired dose.

Preferably, the critical isodose line is not displayed if it is determined that it does not have a predetermined graphical distance from each neighbouring isoline, in particular from an isoline being an isodose line representing a predetermined, in particular desired, dose value, or if it is determined that the critical dose value is less than or equal to a predetermined, in particular desired, dose value. This avoids confusion of the operator by overcrowding the display or a malfunction of the method of displaying the critical isodose line in case too small a value is chosen for c. Preferably, the critical isodose line is not displayed if it does not fulfil the criterion for a graphical distance from its neighbouring isodose line, in particular from the isodose line presenting a predetermined, in particular desired, dose value (more particularly, the next lower dose value for which an associated isoline is to be displayed). Alternatively, according to a further embodiment of the invention, the critical isodose line is displayed irrespective of whether it fulfils any specific criterion for a graphical distance from a neighbouring isoline. In this embodiment, a display of the critical isodose line is thus ensured independent from any conditions relating to the display mode. This supports unconditional information for an operator about the location of any possible hotspots.

The features relating to determining and displaying the critical dose information thus support flexible determination of the critical dose and a manner of display which allows for intuitive deduction of further information when viewed by an operator.

Preferably, the on average equal distances between the isodose lines are determined by fitting isolines to dose values which initially display a Gaussian distribution of dose values at intervals between the minimum and maximum value of dose values described by the dose distribution information. In order to avoid that, when the number of isolines is reduced, isolines which are associated with higher such dose values are no longer contained in the re-determined set of isolines, higher dose values may be given higher weights for a priority of displaying them than lower dose values. In this context, it is noted that a medical operator generally is more interested in displaying information relating to higher dose values due to possible dangers associated with overradiation. The inventive method thus supports safeguarding that such high dose values are given higher priority for being displayed. This also accounts for any non-linearity of the isoline dose intervals after the number of isolines has been re-determined.

Re-determining the number of isoline may for example be desired if the operator varies, in particular reduces, the display area on a display device which is used for displaying the dose distribution information (and, preferably, also the medical image information). For example, an operator may choose to make a corresponding window smaller such that the whole of the image information to be displayed has to be displayed on a smaller absolute area which may lead to resolution problems and may make it impossible or inconvenient for the operator to discern between different isodose lines. Therefore, their spacing has to be adapted to the changed window size. A further condition for re-determining the number of isodose lines in addition to the graphical distance between them may for example be a distance of the operator (in particular, the operator's eyes) from the display device. The distance between the operator and the display device may for example be determined based on taking a photograph of the user from the perspective of the display device and comparing the size of facial features of the operator with their size in a corresponding predetermined image of the operator taken at a known distance from the camera. Alternatively or additionally, re-determining the number of isolines may be based on determining whether the operator squints which may be used as an indication of hampered visual recognition of the displayed image information.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein. The computer on which the aforementioned program is running or into the memory of which the program is loaded preferably comprises a cloud computer.

The program in particular is embodied by an app, i.e. an application which is designed to be run on a mobile, in particular handheld, device such as a smartphone or a tablet computer.

BRIEF DESCRIPTION OF THE DRAWINGS

In the following, an example embodiment of the present invention is described with reference to the Figures, which is merely to be regarded as an example of the invention without limiting the invention to this specific embodiment, wherein.

DETAILED DESCRIPTION

Figure 1:
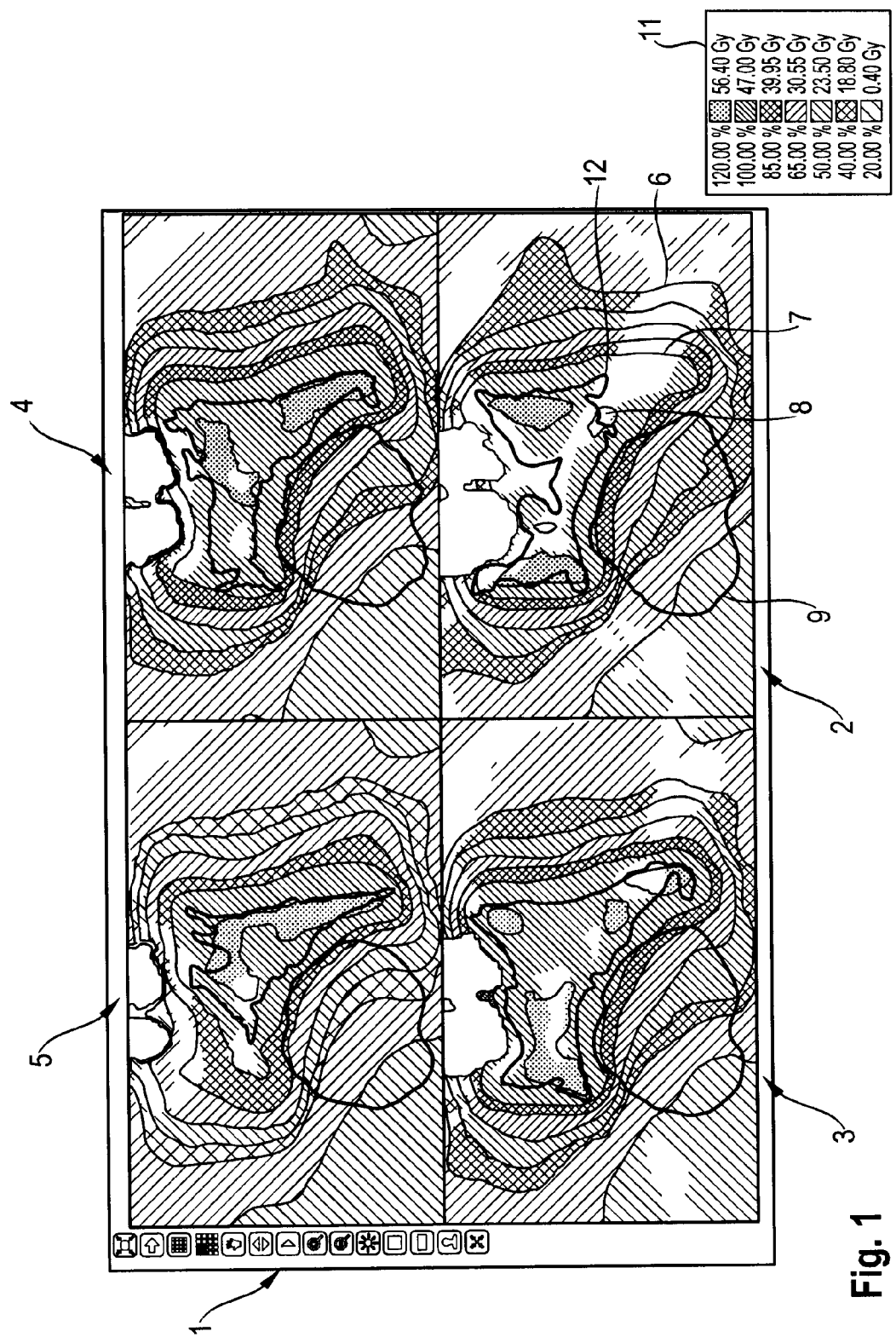
FIG. 1 shows a display of dose distribution information for different anatomical body parts represented by regions of the human brain at the same zoom level.
Figure 2:
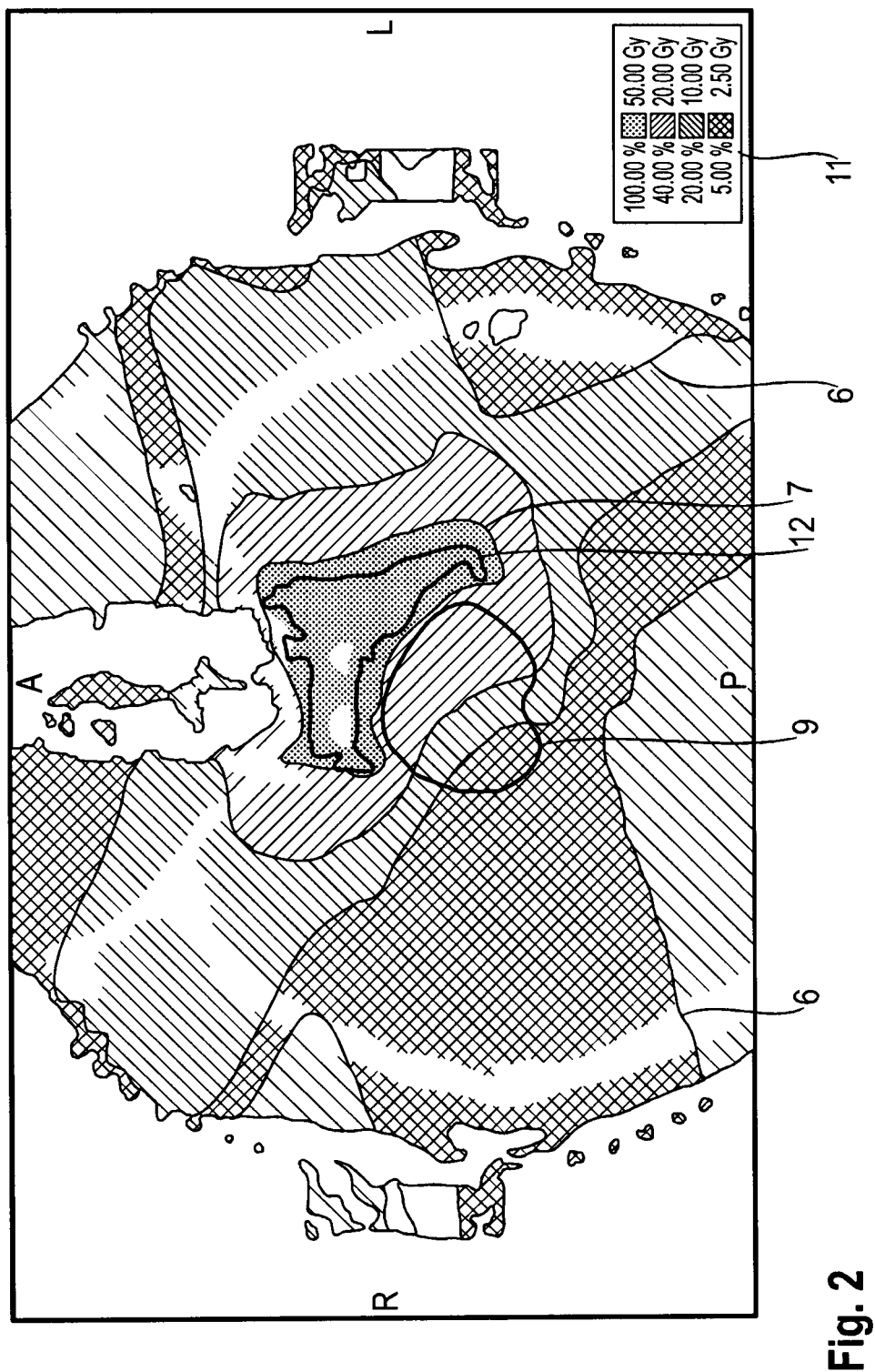
FIGS. 2 to 5 are displays of dose distribution information for the same anatomical body part at different zoom levels.
Figure 3:
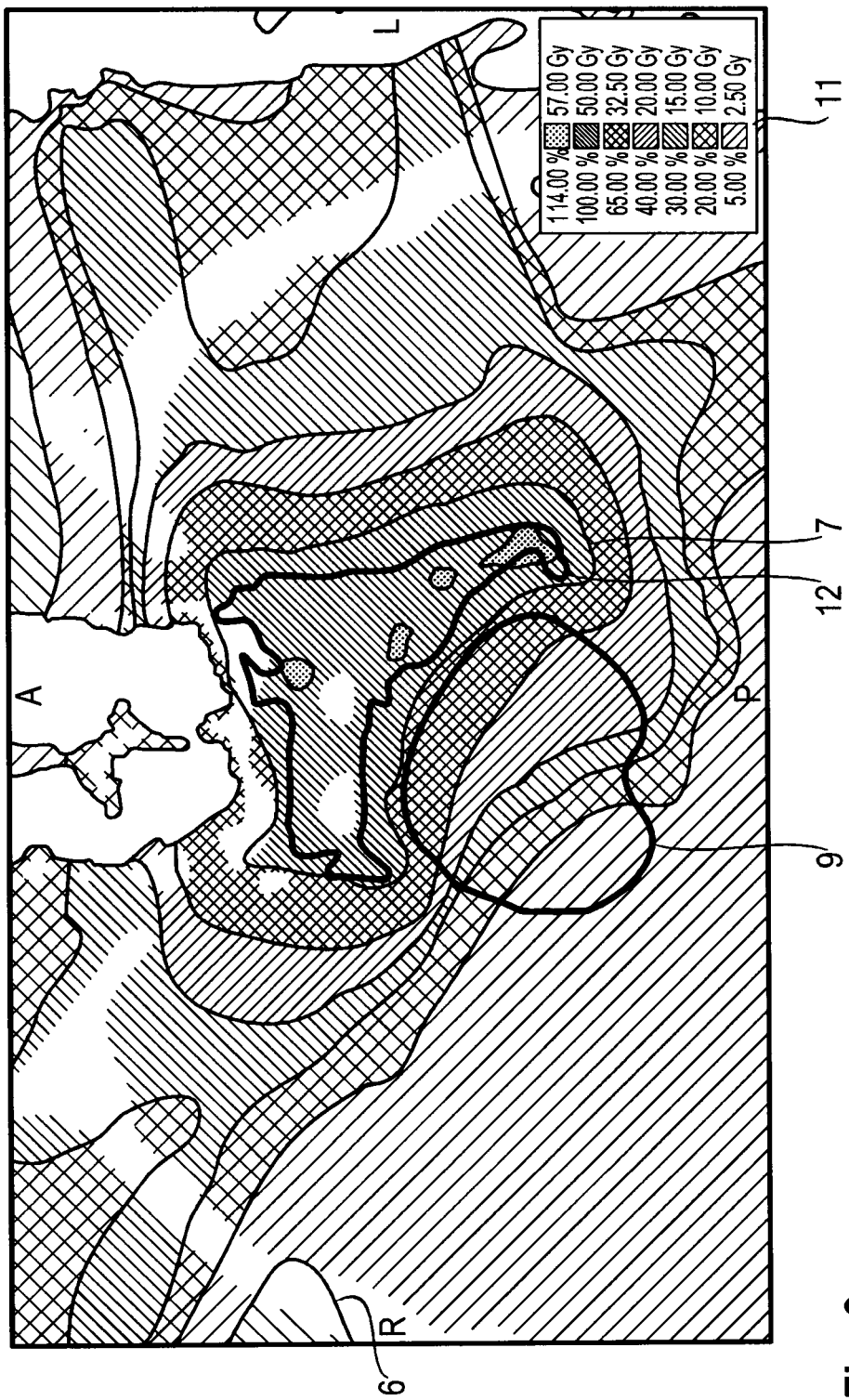
Figure 4:
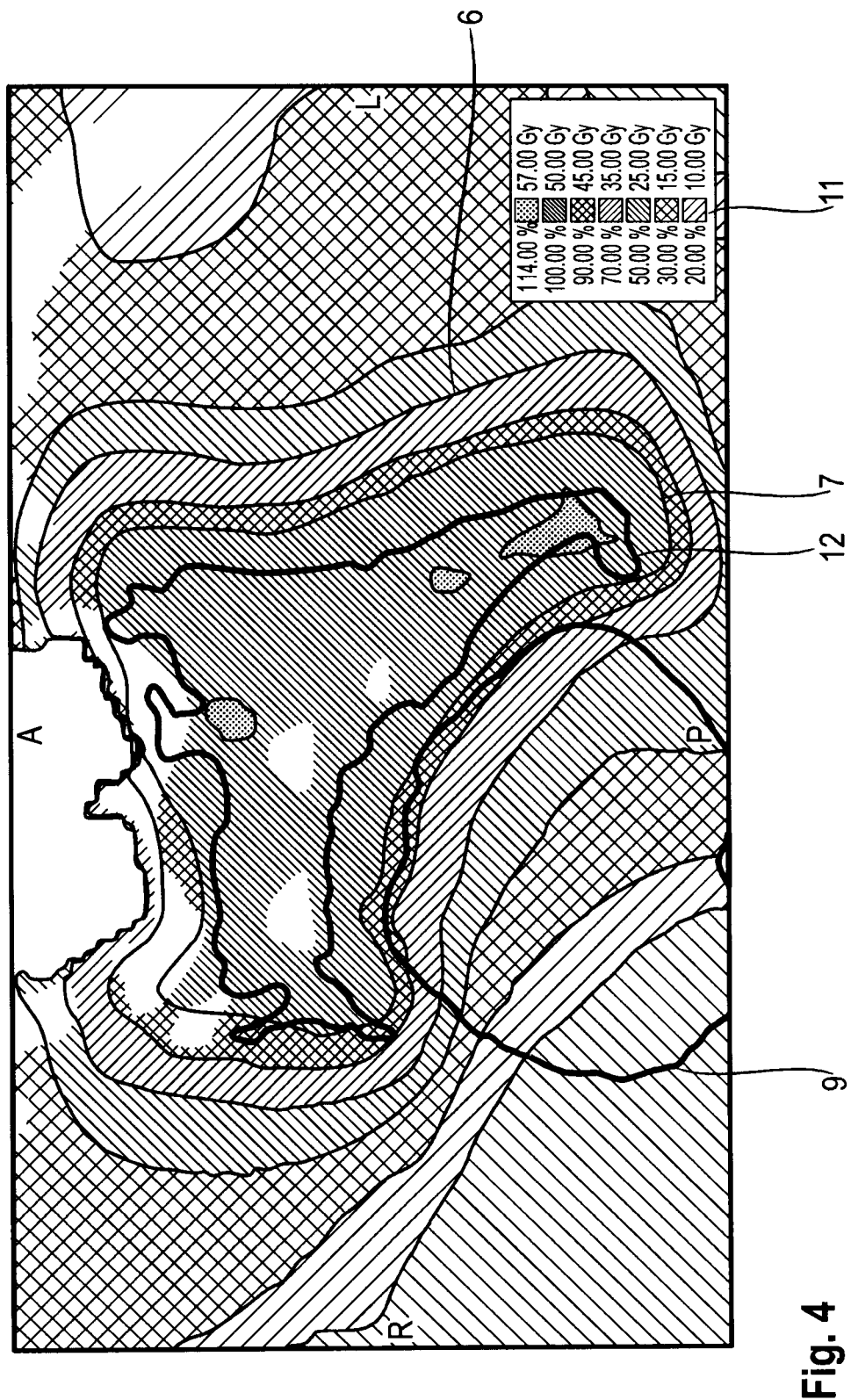
Figure 5:
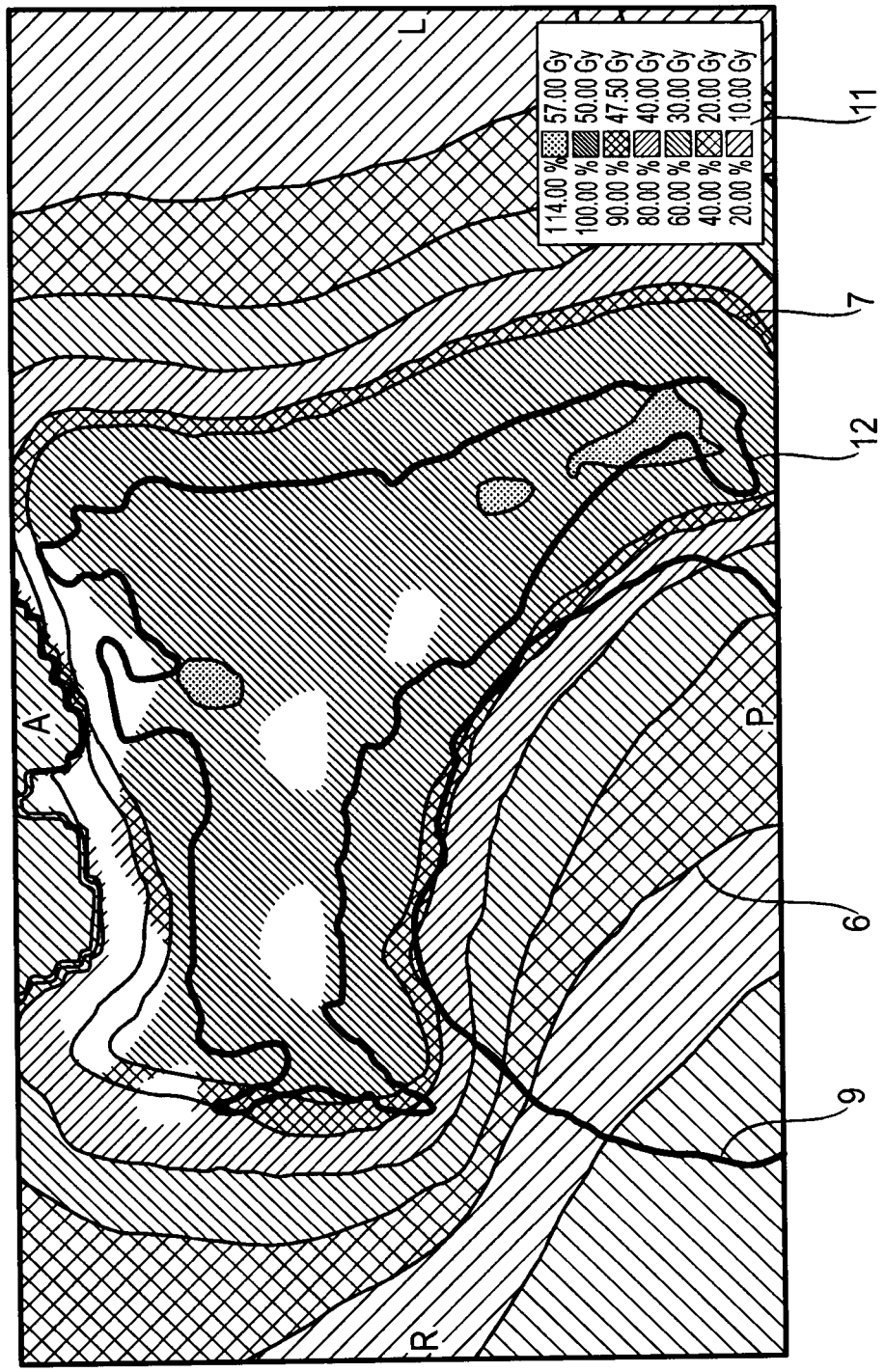

FIG. 1 shows a screenshot taken from an app (i.e. an application executable on a smartphone or tablet computer) which comprises the aforementioned program which, when executed, executes the method as disclosed herein. The graphical output produced by the app is displayed in a window 1 comprising four views 2, 3, 4, 5 of different anatomical regions at the same zoom level. In each of the views 2, 3, 4, 5, medical image information representing parts of the human brain is displayed together with dose distribution information visualized by isodose lines 6. A colour bar 11 which associates different absolute dose values (measured in Gray Gy) is used for illustrating the dose value associated with each of the isodose lines, in particular each isodose line is given a different colour contained in the colour bar 11. The dose values associated with each isodose line, are determined as percentages of the maximum dose contained in the dose distribution information which shall be displayed for the respective medical image information. In the case of FIG. 1, the maximum dose is 120% of a desired dose which is defined to be 100% of the dose used for normalizing the colour bar.

Between neighbouring isolines 6, a colour shading is plotted preferably with a colour value similar to the colour value which is assigned to the respective isodose line of the neighbouring isodose lines representing the lower dose value. With increasing zoom level, the saturation of the colour shading decreases, i.e. the colour shading becomes more transparent in order to allow an operator to recognize more details of the underlying medical image information. A desired dose value is indicated by a desired isodose line 7 which is defined as 100% of dose in accordance with the colour bar 11. Critical isodose lines 8 denoting isolated hotspots are also plotted. The desired dose isodose line 7 encloses a target region 12 defined as the outer limits of a tumour to be irradiated. It is to be noted that the mainstay of the area enclosed by the critical isodose lines 8, i.e. the hotspots, lie within the boundary of the target region 8 and have a comparatively large graphical distance from the desired isodose line 7.

As additional information, the brain stem is visually highlighted by a closed line 9 representing its outer boundaries in the slicing plane in which the image slices illustrated by views 2, 3, 4, 5 are generated. An operator would like to know about the location of the brain stem since the brain stem is an organ at risk, irradiation of which shall avoided as much as possible. In the case of FIG. 1, the brain stem will be irradiated only with dose values below the desired dose value which represents an acceptable situation.

FIGS. 2 to 5 show medical image information of the same anatomical region (in particular, the same slice plane) at different zoom levels, wherein the zoom level increases in steps from FIG. 2 to FIG. 5. The degree of magnification of the image information increases with increasing zoom level. In FIGS. 2 to 5, the same image features as in FIG. 1 are denoted by the same reference signs.

For the different zoom factors used for generating each one of the views of FIGS. 2 to 5, different isodose intervals are assigned to the isodose lines and the graphical distance between each pair of neighbouring isolines is varied according to zoom factor.

Therefore, FIGS. 2 to 5 is an example of how to conveniently display dose distribution information with a medical image information at differing zoom levels.

What is claimed is:

1. A computer-implemented data processing method of determining a distribution of isolines to be used for displaying, on an associated display device, a distribution of a radiation dose in tissue of an associated anatomical body part, the method comprising:
   (a) acquiring dose distribution data comprising dose distribution information describing a distribution of a radiation dose in an associated anatomical body part;
   (b) acquiring display data comprising display information describing a graphical resolution of the associated display device and a predetermined display mode to be applied by the associated display device for displaying the dose distribution information, wherein the display information comprises spacing information describing a predetermined spacing between neighbouring isolines, wherein a number of isolines to be used is determined based on the display information, wherein the predetermined spacing is described as a function of a graphical distance between neighbouring isolines, or as a function of a graphical area between neighbouring isolines; and
   (c) determining, based on the dose distribution data and the display data, isodose data comprising isodose information describing a distribution of isolines to be used for displaying the dose distribution information on the associated display device.

2. The method according to claim 1, comprising:
   acquiring and displaying, on the display device, medical image data comprising medical image information describing the associated anatomical body part;
   displaying, on the associated display device, the dose distribution information as an overlay on the medical image information.

3. The method according to claim 1, wherein the display information comprises graphical resolution information describing a size of an image element, in particular a pixel.

4. The method according to claim 1, wherein the display information comprises spacing information describing a predetermined spacing between neighbouring isolines and wherein the number of isolines is determined such that a spacing between neighbouring isolines is on average the same for all of the isolines, wherein the predetermined spacing is in particular described as a function of distance between neighbouring isolines, in particular average, minimum or maximum distance, or as a function of an area between neighbouring isolines.

5. The method according to claim 1, wherein the number of isolines to be used for displaying is reduced when it is determined, based on the isodose data and the display data, that not all of the isolines have the predetermined spacing from each neighbouring isoline.

6. The method according to claim 1 wherein the number of isolines to be used for displaying is varied, in particular reduced or increased, based on a zoom factor applied to the medical image information.

7. The method according to claim 2, wherein the display information comprises display area information describing a display area to be used for displaying the medical image information and wherein the number of isolines to be used for displaying is only increased if it is determined, based on the display area information, that the display area constitutes a predetermined percentage or absolute amount of a predetermined display area.

8. The method according to claim 1, comprising:
   determining critical dose data comprising critical dose information describing a critical dose which is determined based on determining a predetermined percentage of a difference between a maximum dose value described by the dose distribution information and a predetermined, in particular desired, dose value described by the dose distribution information, and adding the predetermined percentage of the difference to the predetermined, in particular desired, dose value.

9. The method according to claim 8, wherein the predetermined percentage of the difference is 80% of the difference between the maximum dose value described by the dose distribution information and a predetermined, desired, dose value described by the dose distribution information.

10. The method according to claim 9, comprising displaying the critical dose information as a critical isodose line.

11. The method according to claim 10, wherein the critical isodose line is not displayed if it is determined that it does not have a predetermined graphical distance from each neighbouring isoline, in particular from an isoline being an isodose line representing a predetermined, in particular desired, dose value, or if it is determined that the critical dose value is less than or equal to a predetermined, in particular desired, dose value.

12. A computer program embodied on a non-transitory computer readable medium which, when running on a computer or when loaded onto a computer, causes the computer to perform the steps of:
   (a) acquiring dose distribution data comprising dose distribution information describing a distribution of a radiation dose in an associated anatomical body part;
   (b) acquiring display data comprising display information describing a graphical resolution of an associated display device and a predetermined display mode to be applied by the associated display device for displaying the dose distribution information, wherein the display information comprises spacing information describing a predetermined spacing between neighbouring isolines, wherein a number of isolines to be used is determined based on the display information, wherein the predetermined spacing is in particular described as a function of a graphical distance between neighbouring isolines or as a function of a graphical area between neighbouring isolines; and (c) determining, based on the dose distribution data and the display data, isodose data comprising isodose information describing a distribution of isolines to be used for displaying the dose distribution information on the associated display device.

13. The method according to claim 1, wherein the function of distance between neighbouring isolines describes an average, minimum or maximum distance.

* * * * *